US008012277B2

(12) United States Patent
Nicolich et al.

(10) Patent No.: US 8,012,277 B2
(45) Date of Patent: Sep. 6, 2011

(54) IONIC LIQUID AND A METHOD OF SYNTHESIZING AN IONIC LIQUID

(75) Inventors: Steven M. Nicolich, Wyckoff, NJ (US); Alexander J. Paraskos, Ogden, UT (US); Daniel W. Doll, Marriott Slaterville, UT (US); Gary K. Lund, Malad, ID (US); Wendy A. Balas, Piscataway, NJ (US)

(73) Assignees: Alliant Techsystems Inc., Edina, MN (US); Steven M. Nicolich, Wyckoff, NJ (US); Wendy A. Balas, Piscataway, NJ (US)

( * ) Notice: Subject to any disclaimer, the term of this patent is extended or adjusted under 35 U.S.C. 154(b) by 1162 days.

(21) Appl. No.: 11/735,105

(22) Filed: Apr. 13, 2007

(65) Prior Publication Data

US 2008/0251169 A1    Oct. 16, 2008

(51) Int. Cl.
*C06B 47/00* (2006.01)
*C06B 43/00* (2006.01)
*D03D 23/00* (2006.01)
*D03D 43/00* (2006.01)

(52) U.S. Cl. ........ 149/22; 149/1; 149/108.8; 149/109.2; 149/109.4; 149/109.6

(58) Field of Classification Search .................... 149/22, 149/1, 108.8, 109.2, 109.4, 109.6
See application file for complete search history.

(56) References Cited

U.S. PATENT DOCUMENTS

| 4,163,681 | A | 8/1979 | Rothenstein et al. |
| 4,270,435 | A | 6/1981 | Hurst |
| 4,293,541 | A * | 10/1981 | Cairns et al. .................. 514/452 |
| 5,298,654 | A | 3/1994 | DeGuire et al. |
| 6,211,304 | B1 * | 4/2001 | Farooq ........................... 525/403 |
| 6,255,512 | B1 | 7/2001 | Bottaro et al. |
| 6,454,886 | B1 | 9/2002 | Martin et al. |
| 6,509,473 | B1 | 1/2003 | Drake |
| 2005/0123831 | A1 * | 6/2005 | Michot et al. ................. 429/188 |
| 2005/0269001 | A1 * | 12/2005 | Liotta et al. ...................... 149/1 |

FOREIGN PATENT DOCUMENTS

WO    8905789 A1    6/1989

OTHER PUBLICATIONS

Chu-Moyer et al.; J. Med. Chem.; 2002, 45, 511-528.*
U.S. Appl. No. 11/445,910, filed Jun. 2, 2006, entitled "Impact Resistant Explosive Compositions."

* cited by examiner

*Primary Examiner* — James E McDonough
(74) *Attorney, Agent, or Firm* — TraskBritt

(57) ABSTRACT

An ionic liquid is disclosed A precursor composition that comprises at least one ionic liquid and at least one energetic material is also disclosed, as is a method of synthesizing an ionic liquid and a method of desensitizing an explosive composition.

14 Claims, 2 Drawing Sheets ated on Contract No. DAAE30-01-9-0800
IONIC LIQUID AND A METHOD OF SYNTHESIZING AN IONIC LIQUID

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. DAAE30-01-9-0800 awarded by the Department of Defense.

FIELD OF THE INVENTION

The present invention, in various embodiments, relates to ionic liquids and, more specifically, to non-energetic ionic liquids.

BACKGROUND OF THE INVENTION

Ionic liquids have been used in electrochemistry and green chemistry. For these uses, the ionic liquid typically has an imidazolium cation or a pyridinium cation. Ionic liquids have also been investigated to replace trinitrotoluene ("TNT") in melt-pour explosive compositions. In these applications, the ionic liquid is energetic and provides an energy contribution to the composition. Compositions that include the energetic ionic liquids are designed to have an energetic performance greater than or comparable to that of conventional TNT compositions. U.S. Pat. No. 6,509,473 describes energetic triazole salts for use in a propellant. The anion of the salt is a nitrate, perchlorate or dinitramide and the cation is 1,2,4-triazole, 3,4,5-triamino-1,2,4-triazole, or 4-amino-1,2,4-triazole.

U.S. Patent Application No. 2005/0269001 describes an energetic ionic liquid for use in a monopropellant or bipropellant composition. The energetic ionic liquid includes a tetrazolium cation and a nitrate, nitrite, perchlorate, halide, sulfonate, sulfate, borate, phosphate, phosphinate, antimonate, amide, imide, carboxylate, alkyl anion, or coordination complex as an anion. Alternatively, the anion is a tetrazolide and the cation is an ammonium, imidazolium, pyridinium, phosphonium, guanidinium, or uranium cation. The composition optionally includes a nonenergetic ionic liquid.

It would be desirable to develop ionic liquids that desensitize energetic materials. While ionic liquids are commercially available, most of these have corrosive anions (halides, perchlorates) and/or carbon-rich cations and, therefore, are not suitable for use in energetic materials.

BRIEF SUMMARY OF THE INVENTION

One embodiment of the present invention comprises an ionic liquid selected from the group consisting of guanidinium hexafluoroglutarate, aminoguanidinium hexafluoroglutarate, bis(aminoguanidinium) hexafluoroglutarate, bis(hydroxylammonium) hexafluoroglutarate, bis(hydrazinium) hexafluoroglutarate, guanidinium trifluoroacetate, aminoguanidinium trifluoroacetate, triaminoguanidinium trifluoroacetate, hydrazinium trifluoroacetate, 1,2,4-triazolium trifluoroacetate, 3-amino-1,2,4-triazolium trifluoroacetate, 4-amino-1,2,4-triazolium trifluoroacetate, 3,5-diamino-1,2,4-triazolium trifluoroacetate, guanidinium tetrafluorosuccinate, aminoguanidinium tetrafluorosuccinate, guanidinium oxalate, aminoguanidinium oxalate, aminoguanidinium:guanidinium oxalate, bis(guanidinium) malonate, bis(aminoguanidinium) malonate, aminoguanidinium:guanidinium malonate, aminoguanidinium L-tartrate, bis(guanidinium) L-tartrate, bis(aminoguanidinium) L-tartrate, guanidinium glycolate, aminoguanidinium glycolate, triazolium acetate, tetrazolium acetate, diaminotetrazolium acetate, diaminoguanidinium acetate, triaminoguanidinium acetate, bis(aminoguanidinium) DL-malate, tris(aminoguanidinium) nitrilotriacetate, aminoguanidinium mucobromate, aminoguanidinium 5-aminotetrazolate, diaminoguanidinium-hydrochloric acid/urea, guanidinium 5-aminotetrazolate, aminoguanidinium 5-aminotetrazolate, diaminoguanidinium 5-aminotetrazolate, and triaminoguanidinium 5-aminotetrazolate.

Another embodiment of the present invention comprises a method of synthesizing an ionic liquid. The method comprises reacting an anion source with a cation source. The anion source is a compound selected from the group consisting of hexafluoroglutaric acid, trifluoroacetic acid, oxalic acid, L-tartaric acid, DL-malic acid, malonic acid, tetrafluorosuccinic acid, glycolic acid, nitrilotriacetate, mucobromic acid, 5-aminotetrazole, and 5-aminotetrazole monohydrate. The cation source is a compound selected from the group consisting of guanidine carbonate, aminoguanidine bicarbonate, diaminoguanidine-hydrochloric acid, triaminoguanidine-hydrochloric acid, hydroxylamine monohydrate, hydrazine monohydrate, 1,2,4-triazole, 3-amino-1,2,4-triazole, 4-amino-1,2,4-triazole, 3,5-diamino-1,2,4-triazole, ammonia, ammonium chloride, guanylurea, triazine, triazene, alkylamine, alkylammonium chloride, alkylammonium bromide, dialkylamine, dialkylammonium chloride, dialkylammonium bromide, trialkylamine, trialkylammonium chloride, and trialkylammonium bromide.

Another embodiment of the present invention comprises a precursor composition of an explosive composition that comprises at least one ionic liquid and at least one energetic material. The at least one ionic liquid comprises at least one cation and at least one anion. The at least one cation is an ion selected from the group consisting of ammonium, guanidinium, aminoguanidinium, diaminoguanidinium, triaminoguanidinium, hydroxylammonium, hydrazinium, urea, guanylurea, guanizinium, triazanium, triazenium, alkyl ammonium, dialkyl ammonium, trialkyl ammonium, triazolium, 1,2,4-triazolium, 3-amino-1,2,4-triazolium, 4-amino-1,2,4-triazolium, 3,5-diamino-1,2,4-triazolium, tetrazolium, diaminotetrazolium, imidazolium, alkyl imidazolium, morpholinium, pyridinium, a quaternary ammonium ("$R_4N$") compound, a quaternary phosphonium compound, and combinations thereof. The at least one anion is an ion selected from the group consisting of hexafluoroglutarate, trifluoroacetate, acetate, lactate, gluconate, formate, tetrazolate, aminotetrazolate, 5-aminotetrazolate, oxalate, succinate, tetrafluorosuccinate, glycolate, L-tartrate, DL-tartrate, DL-malate, maleate, malonate, nitrilotriacetate, mucobromate, tetrafluoroborate, alkylsulfate, alkylphosphate, bis-trifluorosulfonimide, triflate, tosylate, hexafluorophosphate, a boron-containing compound, and combinations thereof.

Another embodiment of the present invention comprises a method of desensitizing an explosive composition. The method comprises adding at least one energetic material to a melt phase that comprises at least one ionic liquid. The at least one non-energetic ionic liquid comprises at least one cation and at least one anion. The at least one cation is an ion selected from the group consisting of ammonium, guanidinium, aminoguanidinium, diaminoguanidinium, triaminoguanidinium, hydroxylammonium, hydrazinium, urea, guanylurea, guanizinium, triazanium, triazenium, alkyl ammonium, dialkyl ammonium, trialkyl ammonium, triazolium, 1,2,4-triazolium, 3-amino-1,2,4-triazolium, 4-amino-1,2,4-triazolium, 3,5-diamino-1,2,4-triazolium, tetrazolium, diaminotetrazolium, imidazolium, alkyl imidazolium, morpholinium, pyridinium, a quaternary ammonium ("$R_4N$") compound, a quaternary phosphonium compound, and combinations thereof, and the at least one anion is an ion selected from the group consisting of hexafluoroglutarate, trifluoroacetate, acetate, lactate, gluconate, formate, tetrazolate, oxalate, succinate, tetrafluorosuccinate, glycolate, L-tartrate, DL-tartrate, DL-malate, maleate, malonate, nitrilotriacetate, mucobromate, tetrafluoroborate, alkylsulfate, alkylphosphate, bis-trifluoro-sulfonimide, triflate, tosylate, hexafluorophosphate, a boron-containing compound, and combinations thereof.

BRIEF DESCRIPTION OF THE DRAWINGS

While the specification concludes with claims particularly pointing out and distinctly claiming that which is regarded as the present invention, the advantages of this invention may be more readily ascertained from the following description of the invention when read in conjunction the with accompanying drawings in which:

DETAILED DESCRIPTION OF THE INVENTION

Figure 1:
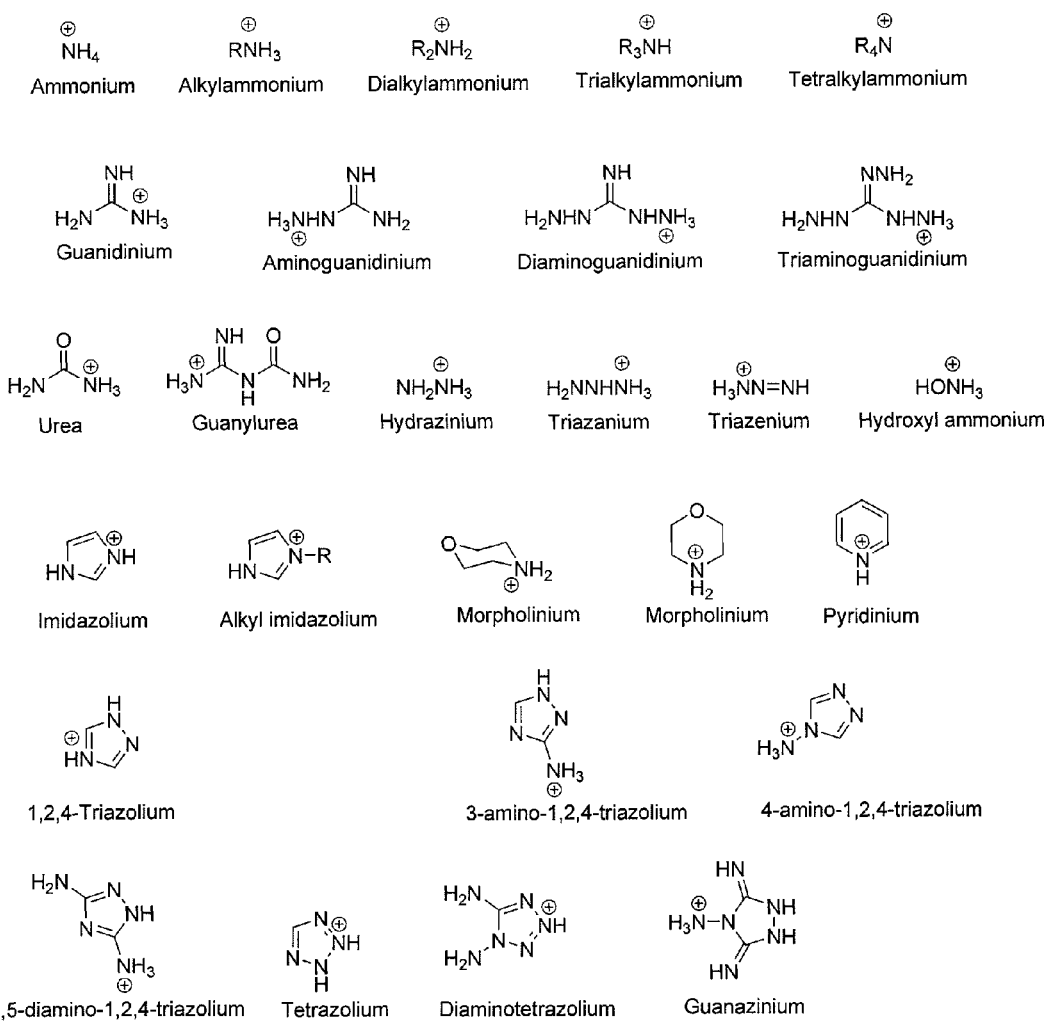
FIG. 1 provides chemical structures of cations present in embodiments of an ionic liquid according to the present invention.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature, or method act indicates that such is contemplated for use in implementation of an embodiment of the invention and such term is used in preference to the more restrictive term "is" so as to avoid any implication that other compatible materials, structures, features, and methods usable in combination therewith should, or must be, excluded.

In one embodiment, a precursor composition includes at least one ionic liquid and at least one energetic material. The precursor composition is used to produce an explosive composition. As used herein, the term "ionic liquid" refers to an ionic material that is in a liquid or molten state at a temperature used to formulate or process the precursor composition of the explosive composition. This temperature is referred to herein as the processing temperature. The processing temperature may depend on the melting point of the ionic liquid. The ionic liquid may be in a nonliquid or a solid state at or near room temperature (from approximately 20° C. to approximately 25° C.) or may be in the liquid state at or near room temperature. For the sake of convenience, the term "ionic liquid" is used herein to refer to the ionic material when the ionic material is in a liquid state or in a solid state. In other words, the term "ionic liquid" refers to the ionic material when the ionic material is at or near the processing temperature of the precursor composition or when the ionic material is solidified in the explosive composition, such as when the ionic material is at or near room temperature. As used herein, the term "precursor composition" refers to a composition that includes the ionic liquid in a liquid state, while the term "explosive composition" refers to a composition that includes the ionic liquid in a solid state.

The at least one ionic liquid is substantially inert or substantially non-energetic. As used herein, the term "non-energetic" means and includes not producing mechanical energy when provided with heat in the absence of an additional oxidizer. In other words, the ionic liquid contributes minimally to the mechanical energy of the explosive composition when provided with heat in the absence of an additional oxidizer. The ionic liquid may be substantially free of conventional energetic moieties or strongly oxidizing anions, such as nitro, nitrate ester, azide, perchlorate, or nitrate moieties. However, the ionic liquid may provide a favorable oxygen to fuel ratio and high density to the explosive composition such that the ionic liquid enables the explosive composition to maintain high shock velocity and high detonation rate. The ionic liquid is compatible with the energetic material and optional ingredients present in the precursor composition. The ionic liquid reduces the sensitivity of the explosive composition to stimuli, such as electrostatic discharge ("ESD"), accidental detonation, impact, friction, or slow or fast cook-off. The ionic liquid may reduce the sensitivity of the explosive composition without substantially affecting the overall energy or performance characteristics of the explosive composition. As such, the explosive composition may have a substantially similar energetic performance to compositions that utilize TNT as the melt phase. In other words, replacing at least a portion of the TNT with the ionic liquid may have substantially no effect on the energetic performance of the explosive composition.

In one embodiment, the ionic liquid is an organic ionic material having a low melting point, a relatively high density, a viscosity less than or equal to the viscosity of TNT (approximately 0.16 kP at 85° C.), and a low vapor pressure (low volatility). The melting point of the ionic liquid may range from approximately 50° C. to approximately 210° C., such as from approximately 80° C. to approximately 110° C. If the ionic liquid has a melting point similar to that of TNT, existing melt-pour facilities may be used to formulate the explosive composition. An ionic liquid having a melting point that falls outside the range of from approximately 80° C. to approximately 110° C. may be used in combination with at least one other ionic liquid, if the at least two ionic liquids form a eutectic mixture having a melting point within the range of from approximately 80° C. to approximately 110° C. An ionic liquid having a melting point that falls outside the range of from approximately 80° C. to approximately 110° C. may also be used if the explosive composition is to be formulated by extruding, pressing, or injection molding. In one embodiment, the explosive composition is formulated by melt-pour techniques.

The density of the ionic liquid is greater than or equal to approximately 1 ml/cm$^3$, such as greater than or equal to approximately 1.2 ml/cm$^3$. For the sake of example only, the density of the ionic liquid may be in a range of from approximately 1.5 ml/cm$^3$ to approximately 2.5 ml/cm$^3$. While the ionic liquid is substantially non-energetic, the high density of the ionic liquid may provide favorable energy contribution to the explosive composition. The density of the explosive composition has the strongest influence on detonation pressure according to the formula:

$$P_D = k\rho^2 NMQ^{1/2},$$

where $P_D$ is the detonation pressure (kbar), $\rho$ is the initial density of the explosive composition, N is the number of moles of gaseous products, M is the molecular weight of the explosive composition, and Q is the chemical energy of detonation. The density of the explosive composition is determined by the density of its components, such as the density of the ionic liquid. Since the density of the explosive composition is a squared term, the higher the density of the explosive composition, the greater the detonation pressure. To provide the desired density, the ionic liquid may include at least one moiety that increases the density of the ionic liquid, such as an alkyl halide, aryl halide, carboxylate, alcohol, or amine moiety. In addition to increasing the density of the ionic liquid, the moiety may provide a desensitizing effect to the explosive composition. Examples of moieties that may be used include, but are not limited to, fluorocarbon moieties, H-bonding moieties, alkyl bromides, or aryl bromides. Since the ionic liquid has a high density, incorporating the ionic liquid into the explosive composition does not adversely affect the overall performance of the explosive composition, avoiding a so-called "dilution" effect in which overall performance may be sacrificed.

While the ionic liquid is an organic ionic material, the ionic liquid may have a low saturated carbon content because saturated carbon atoms consume or utilize oxygen during combustion. The low saturated carbon content minimizes the amount of fuel (i.e. unoxidized carbon) in the explosive composition. As such, the amount of additional oxidizer used in the explosive composition to achieve complete combustion is reduced or minimized. However, if the ionic liquid includes a relatively high saturated carbon content, additional oxidizer may be present in the explosive composition. The ionic liquid may also have a high nitrogen content and a high hydrogen content. The hydrogen atoms may be bound to non-carbon atoms, such as to nitrogen atoms, so that low molecular weight gaseous products are produced when the explosive composition is combusted.

In one embodiment, the ionic liquid includes at least one cation and at least one anion. The cation may be a monocation, dication, trication, tetracation, or polycation. If more than one cation is present in the ionic liquid, each of the cations may be the same or may be different. The cation may have a high density and a low carbon content, a high nitrogen content, and a high hydrogen content. The cation may include, but is not limited to, an ammonium, alkyl ammonium, dialkyl ammonium, trialkyl ammonium, tetraalkyl ammonium, aminoguanidinium ("AG"), diaminoguanidinium ("DAG"), triaminoguanidinium ("TAG"), guanidinium, guanizinium, guanylurea, hydrazinium, hydroxylammonium, imidazolium, alkyl imidazolium, morpholinium, pyridinium, triazanium, triazenium, triazolium, 1,2,4-triazolium, 3-amino-1,2,4-triazolium, 4-amino-1,2,4-triazolium, 3,5-diamino-1,2,4-triazolium, tetrazolium, diaminotetrazolium, urea, or combinations thereof. Chemical structures of the cations are shown in FIG. 1. The cation may also be a quaternary ammonium ("$R_4N$") compound or a quaternary phosphonium ("$R_4P$") compound, where R is hydrogen, a halogen, an alkyl group having from 1 to 20 carbon atoms, an alkyl group having from 1 to 20 carbon atoms and at least one substituent, an aryl group having from 1 to 20 carbon atoms, or an aryl group having from 1 to 20 carbon atoms and at least one substituent. The at least one substituent on the alkyl or aryl group may include, but is not limited to, hydrogen, a halogen, an amino, a nitro, an azide, a hydroxyl, an alkoxyl, or a carbonyl group. The alkyl group may be a straight-chain alkyl group, a branched alkyl group, a cyclic alkyl group, or combinations thereof. The aryl group may be a phenyl, tolyl, or xylyl group or may be a carbocycle or a heterocycle including, but not limited to, furan, pyridine, naphthalene, anthracene, phenanthrene, or triphenylene.

Figure 2:
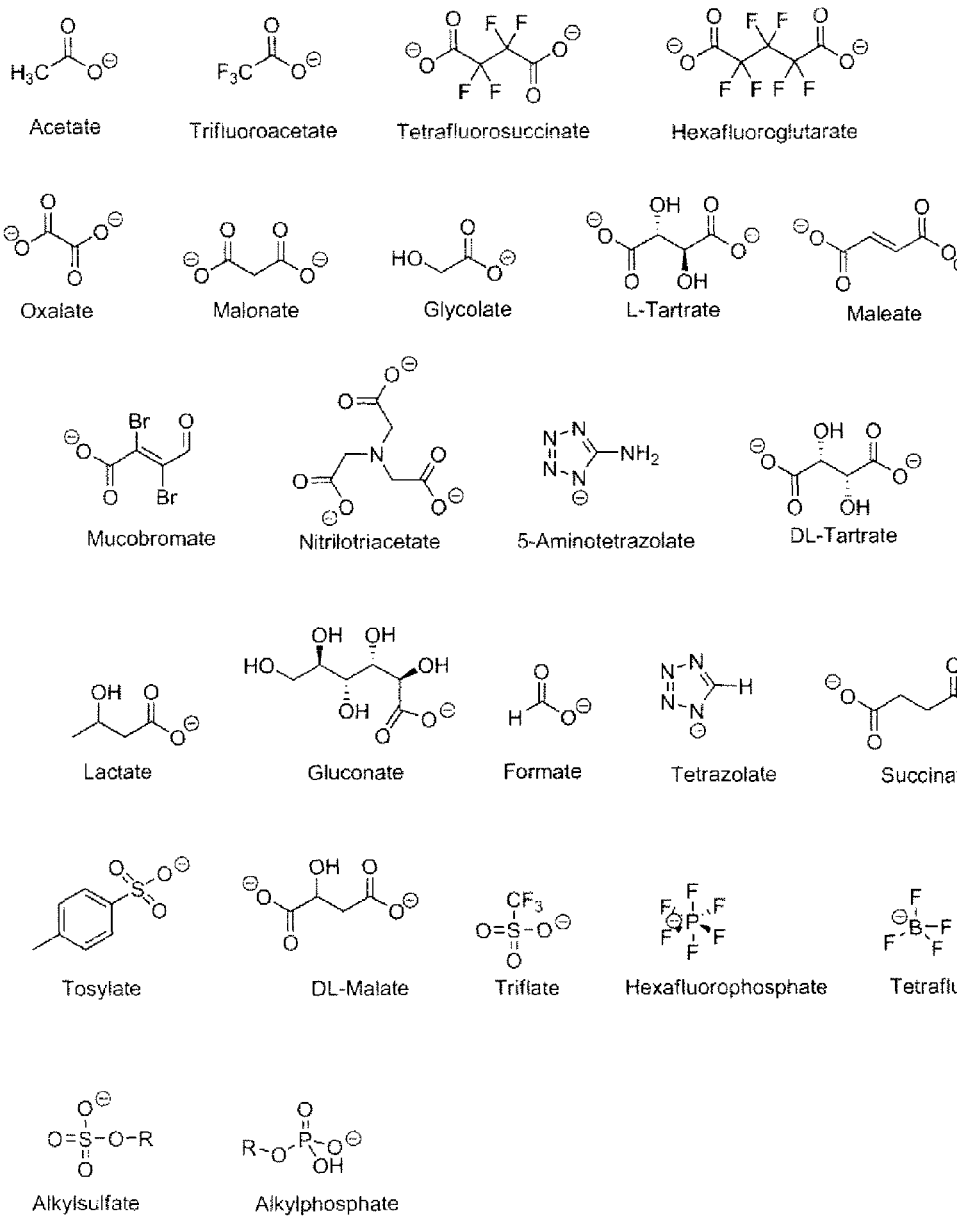
FIG. 2 provides chemical structures of anions present in embodiments of an ionic liquid according to the present invention.

The anion may be substantially non-corrosive and have a high density. As such, the anion may provide a high density to the ionic liquid. The anion may include, but is not limited to, hexafluoroglutarate ("HFG"), trifluoroacetate ("TFA"), acetate, lactate, gluconate, formate, tetrazolate, aminotetrazolate, oxalate, succinate, tetrafluorosuccinate, glycolate, L-tartrate, DL-tartrate, DL-malate, maleate, malonate, nitrilotriacetate, mucobromate, tetrafluoroborate, alkylsulfate, alkylphosphate, bis-trifluorosulfonimide, triflate, tosylate, a boron-containing compound, or hexafluorophosphate. Chemical structures of the cations are illustrated in FIG. 2. The anion may also be a boron-containing compound, such as $(triazole)_3BH$, $(triazole)_4BH$, or $Ar_4B$, where Ar is an aryl group. The aryl group may be a moiety that provides a favorable oxygen to fuel ratio, such as a phenyl, tolyl, or xylyl group or may be a carbocycle, a heterocycle, or polycycle including, but not limited to, furan, pyridine, naphthalene, anthracene, phenanthrene, or triphenylene.

Examples of ionic liquids include, but are not limited to, guanidinium HFG, bis(guanidinium) HFG, aminoguanidinium hexafluoroglutarate ("AGHFG"), bis(aminoguanidinium) hexafluoroglutarate ("BAGHFG"), bis(hydroxylammonium) HFG, bis(hydrazinium) HFG, guanidinium TFA, aminoguanidinium trifluoroacetate ("AGTFA"), triaminoguanidinium trifluoroacetate ("TAGTFA"), hydrazinium TFA, 1,2,4-triazolium TFA, 3-amino-1,2,4-triazolium TFA, 4-amino-1,2,4-triazolium TFA, 3,5-diamino-1,2,4-triazolium TFA, guanidinium tetrafluorosuccinate, AG tetrafluorosuccinate, guanidinium oxalate, AG oxalate, aminoguanidinium:guanidinium oxalate ("AG:G oxalate"), bis(guanidinium) malonate, BAG malonate, aminoguanidinium:guanidinium malonate ("AG:G malonate"), AG L-tartrate, bis(guanidinium) L-tartrate, BAG L-tartrate, bis(aminoguanidinium) DL-tartrate, guanidinium glycolate, aminoguanidinium glycolate ("AG glycolate"), triazolium acetate, diaminotetrazolium acetate, DAG acetate, TAG acetate, BAG DL-malate, tris(aminoguanidinium) nitrilotriacetate, AG mucobromate, DAG-HCl/urea, or combinations thereof. In one embodiment, the ionic liquid is AGTFA, AGHFG, AG L-tartrate, AG:G malonate, AG glycolate, or DAG-HCl/urea. While specific examples herein describe a single ionic liquid in the explosive composition, the explosive composition may include more than one ionic liquid, such as mixtures or combinations of two or more ionic liquids.

If the ionic liquid includes 5-aminotetrazolate as the anion, the ionic liquid may be less energetic (more non-energetic) compared to a conventional ionic liquid, such as an ionic liquid that includes a nitrate, nitrite, or perchlorate anion. However, the ionic liquid having the 5-aminotetrazolate anion may be more energetic than an ionic liquid that includes another anion selected from the anions mentioned above. Examples of cations that may be used in the ionic liquid having 5-aminotetrazolate as the anion include, but are not limited to, guanidinium, AG, DAG, or TAG. In one embodiment, the ionic liquid is guanidinium 5-aminotetrazolate, AG 5-aminotetrazolate, DAG 5-aminotetrazolate, or TAG 5-aminotetrazolate.

The melting point of the ionic liquid may be tailored by appropriately selecting the anion and the cation. For the sake of example only, for an identical anion, an ionic liquid having aminoguanidinium as the cation may have a lower melting point than an ionic liquid having guanidinium as the cation. For the sake of example only, for an identical cation, an ionic liquid having trifluoroacetate as the anion may have a lower melting point than an ionic liquid having hexafluoroglutaric acid as the anion. In addition, an ionic liquid having a lower melting point may be achieved by having a low degree of symmetry between the anion and the cation. The melting point of the ionic liquid may be further tailored by altering the chemical structure of at least one of the anion and the cation. For instance, to increase or decrease the melting point, at least one of the moieties previously described as increasing the density of the ionic liquid or providing a desensitizing effect to the explosive composition may be incorporated into at least one of the anion and the cation. The melting point may also be adjusted by incorporating a substituent onto at least one of the cation and the anion. For instance, for a specific cation, the ionic liquid may have a higher melting point if a halide, such as fluorine, is used as the anion than if tetrafluoroborate or hexafluorophosphate is used as the anion.

Melting points and carbon ("C"), hydrogen ("H"), and nitrogen ("N") contents for specific ionic liquids are shown in Table 1.

TABLE 1

Elemental analyses and melting points for ionic liquids.

| Ionic liquid | C, H, N Expected (Observed) | Melting point (° C.) |
| --- | --- | --- |
| Bis(guanidinium) hexafluoroglutarate | 23.47 (23.61), 3.38 (3.17), 23.46 (21.03) | 170-175 |
| Bis(aminoguanidinium) hexafluoroglutarate | 21.66 (22.48), 3.63 (3.87), 28.86 (28.78) | 104-114 |
| Bis(hydroxylammonium) hexafluoroglutarate | 19.62 (19.66), 2.63 (2.52), 9.15 (9.25) | 107-110 |
| Bis(hydrazinium) hexafluoroglutarate | 19.74 (19.88), 3.31 (3.16), 18.42 (18.26) | 142-146 |
| Guanidinium trifluoroacetate | 20.82 (20.82), 3.49 (3.08), 24.28 (24.13) | 155-160 |
| Aminoguanidinium trifluoroacetate | 19.15 (19.11), 3.75 (3.63), 29.78 (29.74) | 55-60 |
| Triaminoguanidinium trifluoroacetate | 16.52 (15.96), 4.16 (4.38), 38.53 (35.63) | 72 |
| Hydrazinium trifluoroacetate | 16.45 (16.45), 3.45 (3.28), 19.18 (19.19) | Liquid at room temperature |
| 1,2,4-triazolium TFA | 26.24 (26.44), 2.20 (2.35), 22.95 (24.73) | 77 |
| 3-amino-1,2,4-triazolium TFA | 24.25 (24.35), 2.54 (2.52), 28.28 (28.75) | 138 |
| 4-amino-1,2,4-triazolium TFA | 24.25 (23.09) 2.54 (3.14), 28.28 (28.31) | Liquid at room temperature |
| 3,5-diamino-1,2,4-triazolium TFA | 22.54 (22.47), 2.84 (2.72), 32.86 (32.66) | 138 |
| Guanidinium tetrafluorosuccinate | 23.38 (23.27), 3.92 (3.59), 27.27 (27.51) | 175-185 |
| Aminoguanidinium tetrafluorosuccinate | 21.31 (20.54), 4.17 (4.65), 33.13 (34.08) | 135-140 |
| Guanidinium oxalate | 23.08 (22.65), 5.81 (6.08), 40.37 (39.37) | 155-160 |
| Aminoguanidinium oxalate | 20.17 (20.28), 5.92 (6.03), 47.04 (47.88) | 195-205 |
| 60:40 Aminoguanidinium:guanidinium oxalate | 21.24 (20.71), 5.88 (5.92), 44.58 (43.06) | 78 |
| Bis(guanidinium) malonate | 27.03 (27.11), 6.35 (6.44), 37.82 (38.47) | 175-180 |
| 60:40 Aminoguanidinium:guanidinium malonate | 25.00 (25.10), 6.38 (6.50), 41.98 (41.61) | 98 |
| Bis(aminoguanidinium) malonate | 23.81 (23.96), 6.39 (6.54), 44.42 (44.92) | 140-150 |
| Bis(guanidinium) L-tartrate | 26.87 (26.22), 6.01 (5.65), 31.33 (31.14) | 152-156 |
| Bis(aminoguanidinium) L-tartrate | 24.16 (25.35), 6.08 (5.30), 37.57 (38.81) | 55 (DSC onset) |
| Bis(aminoguanidinium) DL-tartrate | n/a | 183-185 |
| Guanidinium glycolate | 26.67 (27.45), 6.71 (6.49), 31.10 (30.64) | 54 (DSC onset) |
| Aminoguanidinium glycolate | 24.00 (26.12), 6.71 (6.20), 37.32 (40.25) | 88 (DSC onset) |
| Bis(aminoguanidinium) DL-malate | 25.53 (25.83), 6.43 (6.31), 39.70 (39.93) | 142-146 |
| Tris(aminoguanidinium) nitrilotriacetate | 26.15 (25.56), 6.58 (6.08), 44.05 (40.34) | 144-154 |
| Aminoguanidinium mucobromate | 18.09 (18.99), 2.43 (1.00), 16.88 (17.84) | 210 (decomp) |
| Aminoguanidinium 5-aminotetrazolate | 15.09 (15.20), 5.70 (5.68), 79.21 (74.88) | 94 |

In one embodiment, the ionic liquid is synthesized by reacting a source of the anion with a source of the cation. For the sake of example only, the HFG anion may be obtained from hexafluoroglutaric acid, the TFA anion may be obtained from trifluoroacetic acid, the oxalate anion may be obtained from oxalic acid, the L-tartrate anion may be obtained from L-tartaric acid, the DL-malic acid anion may be obtained from DL-malic acid, the malonate anion may be obtained from malonic acid, the tetrafluorosuccinate anion may be obtained from tetrafluorosuccinic acid, the glycolate anion may be obtained from glycolic acid, the nitrilotriacetate anion may be obtained from nitrilotriacetate, the mucobromate anion may be obtained from mucobromic acid, and the 5-aminotetrazolate anion may be obtained from 5-aminotetrazole or 5-aminotetrazole monohydrate. For the sake of example only, the guanidinium cation may be obtained from guanidine carbonate, the AG cation or the tris(aminoguanidinium) cation may be obtained from aminoguanidine bicarbonate, the DAG cation may be obtained from diaminoguanidine-HCl, the TAG cation may be obtained from triaminoguanidine-HCl, the hydroxylammonium cation or the bis(hydroxylammonium) cation may be obtained from hydroxylamine monohydrate, the hydrazinium cation or the bis(hydrazinium) cation may be obtained from hydrazine monohydrate, the 1,2,4-triazolium cation may be obtained from 1,2,4-triazole, the 3-amino-1,2,4-triazolium cation may be obtained from 3-amino-1,2,4-triazole, the 4-amino-1,2,4-triazolium cation may be obtained from 4-amino-1,2,4-triazole, the 3,5-diamino-1,2,4-triazolium cation may be obtained from 3,5-diamino-1,2,4-triazole, the ammonium cation may be obtained from ammonia or ammonium chloride, the guanylurea cation may be obtained from guanylurea, the triazinium cation may be obtained from triazine, the triazenium cation may be obtained from triazene, the alkyl ammonium cation may be obtained from alkylamine, alkylammonium chloride, or alkylammonium bromide, the dialkyl ammonium cation may be obtained from dialkylamine, dialkylammonium chloride, or dialkylammonium bromide, and the trialkyl ammonium cation may be obtained from trialkylamine, trialkylammonium chloride, or trialkylammonium bromide.

Stoichiometric amounts of the source of the anion and the source of the cation may be reacted. In one embodiment, an excess of at least one of these reactants may be used. These reagents may be combined at ambient temperature and pressure, above ambient temperature and pressure, or below ambient temperature and pressure. The reaction may produce crystals (at room temperature) of the ionic liquid.

The ionic liquid may be synthesized in quantitative yields neat or using water as a solvent. Depending on the ionic liquid being synthesized, no byproducts (other than water) are formed, carbon dioxide and water are formed as byproducts, sodium chloride or potassium chloride is formed as a byproduct, or ammonia and water are formed as byproducts. Gaseous byproducts, such as carbon dioxide and ammonia, may be evolved, water may be removed in vacuo, and solid byproducts, such as sodium chloride or potassium chloride, may be filtered or otherwise removed. Since the byproducts produced by synthesizing the ionic liquid are relatively innocuous, the ionic liquid may be synthesized with minimal environmental impact. In addition, since any byproducts may be easily removed, substantially pure ionic liquid may be synthesized without extensive purification. The synthesis of the ionic liquid is easily scalable to enable production of large quantities of the ionic liquid.

Guanidinium salts of carboxylates may be synthesized by reacting a corresponding carboxylic acid with guanidine carbonate. The carboxylic acid may be a solid or liquid at room temperature. If the carboxylic acid is a solid at room temperature, the carboxylic acid may be dissolved in a minimal amount of distilled water. Alternatively, if the carboxylic acid has a low melting point, the carboxylic acid may be heated to a temperature greater than or approximately equal to its melting point. The carboxylic acid may be reacted with approximately one-half of a molar equivalent of guanidine carbonate for each carboxylic acid moiety in the carboxylic acid. Carbon dioxide is evolved as the reaction proceeds. The reaction is stirred overnight and water (solvent or byproduct) is removed in vacuo at elevated temperature, such as at approximately 90° C., to yield crystals of the product.

Aminoguanidinium salts of carboxylates may be synthesized by reacting the corresponding carboxylic acid with aminoguanidine bicarbonate. The carboxylic acid may be a solid or liquid at room temperature. If the carboxylic acid is a solid at room temperature, the carboxylic acid may be dissolved in a minimal amount of distilled water. Alternatively, if the carboxylic acid has a low melting point, the carboxylic acid may be heated to a temperature greater than or approximately equal to its melting point. The carboxylic acid in the liquid state may be reacted with approximately one molar equivalent of aminoguanidine bicarbonate for each carboxylic acid moiety in the carboxylic acid. Carbon dioxide is evolved as the reaction proceeds. The reaction is stirred overnight and water (solvent or byproduct) is removed in vacuo at elevated temperature, such as at approximately 90° C., to yield crystals of the product.

Hydrazinium salts of carboxylates may be synthesized by reacting the corresponding carboxylic acid with hydrazine monohydrate. To produce a hydrazinium compound, molar equivalents of the hydrazine monohydrate and the carboxylic acid may be reacted. To produce a bis(hydrazinium) compound, approximately two molar equivalents of the hydrazine monohydrate may be reacted for each carboxylic acid moiety in the carboxylic acid. The hydrazine monohydrate may be added to a minimal amount of distilled water with stirring at room temperature. The carboxylic acid may then be added with stirring. No byproducts, other than water, are formed during the reaction. The reaction is stirred overnight and water (solvent or byproduct) is removed in vacuo at elevated temperature, such as at approximately 80° C., to yield crystals of the product or the product as a liquid.

Hydroxylammonium salts of carboxylates may be synthesized by reacting the corresponding carboxylic acid with an aqueous solution of hydroxylamine. One molar equivalent of the hydroxylamine may be added for each carboxylic acid moiety in the carboxylic acid. The hydroxylamine may be diluted with distilled water and the carboxylic acid added with stirring at room temperature. No byproducts, other than water, are formed during the reaction. The reaction is stirred at room temperature and water (solvent or byproduct) is removed in vacuo at elevated temperature, such as at approximately 90° C., to yield crystals of the product.

In addition to the ionic liquid, the precursor composition may include at least one energetic material, such as a nitramine or a nitrocarbon. The ionic liquid may desensitize the energetic material without significantly diluting the overall energy of the explosive composition. The energetic material may include, but is not limited to, dinitrotoluene ("DNT"), TNT, cyclotetramethylene tetranitramine ("HMX"), cyclo-1,3,5-trimethylene-2,4,6-trinitramine ("RDX"), hexanitrohexaazaisowurtzitane ("CL-20"), triaminotrinitrobenzene (TATB), nitrotriazolone (NTO), Composition B (60-64% RDX and 36-40% TNT), 4,10-dinitro-2,6,8,12-tetraoxa-4,10-diazatetracyclo[5.5.0.0$^{5,9}$.0$^{3,11}$]dodecane ("TEX"), 1,3,3-trinitroazetine ("TNAZ") ammonium dinitramide ("ADN"), or combinations thereof. The ionic liquid may account for from approximately 13% by weight ("wt %") of a total weight of the precursor composition to approximately 75 wt % of the total weight of the precursor composition and the energetic material may account for from approximately 25 wt % of the total weight of the precursor composition to approximately 90 wt % of the total weight of the precursor composition. In one embodiment, the ionic liquid accounts for from approximately 30% by weight to 55% by weight of the total weight of the precursor composition and the energetic material accounts for from approximately 45% by weight to 70% by weight of the total weight of the precursor composition.

Additional ingredients may, optionally, be present in the precursor composition. Such optional ingredients include, but are not limited to, at least one oxidizer or at least one metal or metal-containing compound. The additional ingredients in the precursor composition may provide desired performance properties to the explosive composition or may aid in processing. The oxidizer may be a nitrate, perchlorate, or oxide, such as an alkali or alkaline metal nitrate, an alkali or alkaline metal perchlorate, or an alkaline metal peroxide. The oxidizer may include, but is not limited to, ammonium nitrate ("AN"), ammonium perchlorate ("AP"), sodium nitrate ("SN"), potassium nitrate ("KN"), lithium nitrate, rubidium nitrate, cesium nitrate, lithium perchlorate, sodium perchlorate, potassium perchlorate ("KP"), rubidium perchlorate, cesium perchlorate, magnesium perchlorate, calcium perchlorate, strontium perchlorate, barium perchlorate, barium peroxide, strontium peroxide, copper oxide, and combinations thereof. The metal or metal-containing compound may include, but is not limited to, aluminum, nickel, magnesium, silicon, boron, beryllium, zirconium, hafnium, zinc, tungsten, molybdenum, titanium, aluminum hydride ("AlH$_3$" or alane), magnesium hydride ("MgH$_2$"), borane compounds ("BH$_3$"), or combinations thereof. If present, these ingredients may account for from approximately 0 wt % to approximately 40 wt % of the total weight of the precursor composition.

The additional ingredients may also include, but are not limited to, sugars, processing aids, surfactants, binders, energetic polymers, inert polymers, fluoropolymers, thermal stabilizers, plasticizers, or combinations thereof. Such ingredients are known in the art and, therefore, are not described in detail herein.

The ionic liquid, the energetic material, and the additional ingredients, if present, may be combined as known in the art, forming the precursor composition. Since the ionic liquid has a low melting point, the ionic liquid may function as a melt phase for the precursor composition. The ionic liquid may be added to a conventional melt kettle and heated to the processing temperature, which is a temperature greater than or approximately equal to the melting point of the ionic liquid, forming a low viscosity, liquid state. The processing temperature may be from approximately 10° C. to approximately 20° C. greater than the melting point of the ionic liquid. The processing temperature may be in the range of from approximately 75° C. to approximately 115° C., such as in the range of from approximately 85° C. to approximately 105° C. The ionic liquid may provide substantially all of the melt phase of the precursor composition. However, if the energetic material is also a liquid at the processing temperature, the energetic material may form at least a portion of the melt phase. The energetic material and additional ingredients, if present, may be incorporated into the melt phase and combined to form a substantially homogenous mixture of the precursor composition. The energetic material and additional ingredients may be suspended in the ionic liquid. However, if the energetic material is TNT, the TNT may form a miscible mixture with the ionic liquid. The viscosity of the precursor composition at the processing temperature may be sufficiently low such that the precursor composition may be poured into an explosive device or ordnance. For instance, the precursor composition may have a viscosity of less than or equal to approximately 5 kP at the processing temperature.

The precursor composition may be used as an explosive fill material in conventional explosive devices or ordnance, such as in mortars, artillery, grenades, mines, or bombs. The precursor composition may be loaded into the explosive device or ordnance by conventional techniques, which are not described in detail herein. For the sake of example only, the precursor composition may be melt-poured into the explosive device or ordnance. The precursor composition may be poured into the explosive device or ordnance, cooled below the melting point of the ionic liquid, and solidified. As such, the explosive device or ordnance may be substantially filled with the explosive composition that includes the at least one ionic liquid and the at least one energetic material. Since the ionic liquid is a liquid at the processing temperature, the precursor composition may be used to fill irregular volumes in the explosive device or ordnance without forming voids.

In addition to melt-pour techniques, the precursor composition may also be pressed, extruded, or injection molded. To produce a pressed, extruded, injection molded, or cast-cure explosive composition, the ionic liquid, energetic material, and any additional ingredients (if present) may be combined as known in the art. The explosive composition may then be pressed, extruded, injection molded, or cast and cured cured, as desired. The explosive composition is substantially homogeneous.

The following examples serve to explain embodiments of the present invention in more detail. These examples are not to be construed as being exhaustive or exclusive as to the scope of this invention.

EXAMPLES

Example 1

Synthesis of AG Glycolate

Glycolic acid (253.2 g, 3.34 mol) was weighed into a 2-liter beaker and dissolved in 1500 ml of distilled water with stirring Aminoguanidine bicarbonate (454.8 g, 3.34 mol) was added to the beaker in portions with stirring to avoid bubbling over the sides of the beaker due to the evolution of carbon dioxide. The reaction was stirred at room temperature overnight (approximately 24 hours) at which time all of the solids had dissolved. The water was removed from the reaction mixture in vacuo with heating to approximately 90° C. for 4 hours. The product was recovered as a crystalline white solid.

Example 2

Synthesis of AG 5-AT 5-aminotetrazole monohydrate (250.0 g, 2.425 mol) was weighed into a 2-liter beaker and dissolved in 1500 ml of distilled water with stirring. Aminoguanidine bicarbonate (330.1 g, 2.425 mol) was added to the beaker with stirring at room temperature. Carbon dioxide slowly evolved. The reaction was stirred at room temperature for 48 hours, at which time most of the solids had dissolved. The water was removed from the reaction mixture in vacuo with heating to approximately 90° C. for 4 hours. The product was recovered as a crystalline white solid.

In an alternate synthesis, 5-aminotetrazole (250.0 g, 2.425 mol) was weighed into a 2-liter beaker and dissolved in 1500 ml of distilled water with stirring. Aminoguanidine bicarbonate (330.1 g, 2.425 mol) was added to the beaker with stirring at room temperature. Carbon dioxide slowly evolved. The reaction was stirred at room temperature for 48 hours, at which time most of the solids had dissolved. The water was removed from the reaction mixture in vacuo with heating to approximately 90° C. for 4 hours. The product was recovered as a crystalline white solid.

Example 3

Synthesis of AGTFA

Aminoguanidine bicarbonate (906.2 g, 6.66 mold was placed in a 4-liter beaker. Trifluoroacetic acid (760.2 g, 6.66 mol) was added in three, roughly equal, increments with stirring after each addition to avoid bubbling over the sides of the beaker due to the evolution of carbon dioxide during the reaction. The beaker was placed in a vacuum oven at 70° C. to promote the reaction until carbon dioxide evolution was no longer observed (approximately 2 hours). The water was removed from the reaction mixture in vacuo with heating to approximately 90° C. for 4 hours. The product was recovered as a crystalline, slightly off-white solid.

In an alternate synthesis, AGTFA was synthesized by adding trifluoroacetic acid (2.0 ml, 2.96 g, 25.96 mmol) to 50 ml of distilled water in a 250-ml round-bottom flask with stirring. Aminoguanidine bicarbonate (3.53 g, 25.96 mmol) was added at room temperature to the round-bottom flask in portions with stirring as to avoid bubbling over the sides of the flask due to the evolution of carbon dioxide. The reaction was stirred at room temperature overnight. The water was removed in vacuo with heating to approximately 90° C. for 4 hours. The product was recovered as a crystalline, slightly off-white solid.

Example 4

Synthesis of 60:40 AG:Guanidinium Oxalate

Oxalic acid (200.0 g, 2.22 mol) was weighed into a 2-liter beaker with a magnetic stir bar and dissolved in 1500 ml of distilled water. Aminoguanidine bicarbonate (362.8 g, 2.67 mol) and guanidine carbonate (160.1 g, 0.89 mol) were added in portions with stirring as to avoid bubbling over the sides of the beaker due to the evolution of carbon dioxide during the reaction. The reaction was stirred at room temperature overnight (approximately 24 hours). The water was removed from the reaction mixture in vacuo with heating to approximately 90° C. for 4 hours. The product was recovered as a crystalline white solid.

Example 5

Synthesis of 60:40 AG:Guanidinium Malonate

Malonic acid (200.0 g, 1.922 mol) was weighed into a 2-liter beaker with a magnetic stir bar and dissolved in 1500 ml of distilled water. Aminoguanidine bicarbonate (313.9 g, 2.31 mol) and guanidine carbonate (138.5 g, 0.769 mol) were added in portions with stirring as to avoid bubbling over the sides of the beaker due to the evolution of carbon dioxide during the reaction. The reaction was stirred at room temperature overnight (approximately 24 hours). The water was removed from the reaction mixture in vacuo with heating to approximately 90° C. for 4 hours. The product was recovered as a crystalline white solid.

Example 6

Synthesis of BAGHFG

Hexafluoroglutaric acid (11.14 g, 46.41 mmol) was weighed into a 250-ml round-bottom flask with a magnetic stir bar and dissolved in 50 ml of distilled water. Aminoguanidine bicarbonate (12.63 g, 92.81 mmol) was added in portions with stirring to avoid bubbling over the sides of the flask due to the evolution of carbon dioxide. The reaction was stirred at room temperature overnight (approximately 24 hours). The water was removed from the reaction mixture in vacuo with heating to approximately 90° C. for 4 hours. The product was recovered as a crystalline white solid.

Example 7

Synthesis of Diaminoguanidinium/Urea (1:2 mol % Eutectic Mixture)

Diaminoguanidinium hydrochloride (13.0 g, 103.5 mmol) and urea (12.4 g, 207.1 mmol) were placed in a flask with stirring. The flask was heated to 10° C. and stirred until a melt was formed, at which time the mixture was cooled to room temperature and the product collected as a white solid.

Example 8

Synthesis of DAGTFA

Diaminoguanidinium trifluoroacetate is synthesized by reacting diaminoguanidine hydrochloride and sodium trifluoroacetate in acetone or acetonitrile. Sodium chloride is produced as a byproduct of the reaction and is removed, producing the diaminoguanidinium trifluoroacetate.

Example 9

Synthesis of Guanidinium HFG

Hexafluoroglutaric acid (500 mg, 2.08 mmol) was weighed into a 50-ml round-bottom flask with a magnetic stir bar and dissolved in 5 ml of distilled water. Guanidine carbonate (375 mg, 2.08 mmol) was added in portions with stirring to avoid bubbling over the sides of the flask due to the evolution of carbon dioxide. The reaction was stirred at room temperature overnight (approximately 24 hours). The water was removed from the reaction mixture in vacuo with heating to approximately 90° C. for 4 hours. The product was recovered as a crystalline white solid.

Example 10

Synthesis of Bis(hydrazinium) HFG

Hydrazine monohydrate (0.50 ml, 10.31 mmol) was added via syringe to a 50-ml round-bottom flask containing 5 ml of distilled water with stirring at room temperature. Hexafluoroglutaric acid (1.24 g, 5.15 mmol) was added and the reaction was stirred at room temperature for 2 hours. The water was removed in vacuo with heating to 80° C., yielding 1.5 g of bis(hydrazinium) HFG as a white solid.

Example 11

Synthesis of Hydrazinium TFA

Hydrazine monohydrate (4.41 ml, 90.9 mmol) was added via syringe to a 250-ml round-bottom flask containing 50 ml of distilled water with stirring at room temperature. Trifluoroacetic acid (7.0 ml, 90.9 mmol) was added via syringe and the reaction was stirred at room temperature overnight. The water was removed in vacuo with heating to 80° C., yielding product as a colorless liquid.

Example 12

Synthesis of Bis(hydroxylammonium) HFG

Hydroxylamine solution (1.0 g, 50% in $H_2O$, 15.14 mmol) was added to a flask with stirring and diluted with 5 ml of distilled water. Hexafluoroglutaric acid (1.82 g, 7.57 mmol) was added and the reaction was stirred at room temperature overnight. The water was removed in vacuo with heating to 90° C., resulting in 2.2 g of bis(hydroxylammonium) HFG as a white solid.

Example 13

Synthesis of Diaminoguanidinium Acetate

Diaminoguanidinium acetate is synthesized by reacting diaminoguanidine hydrochloride and sodium acetate in acetone or acetonitrile. Sodium chloride is produced as a byproduct of the reaction and is removed, producing the diaminoguanidinium acetate.

Example 14

Synthesis of Triaminoguanidinium Acetate

Triaminoguanidinium acetate is synthesized by reacting triaminoguanidine hydrochloride and sodium acetate in acetone or acetonitrile. Sodium chloride is produced as a byproduct of the reaction and is removed, producing the triaminoguanidinium acetate.

Example 15

Synthesis of Triaminoguanidinium TFA

Guanidinium trifluoroacetate (5.00 g, 28.89 mmol) was dissolved in 20 ml of distilled water in a 50-ml round-bottom flask with a stir bar. Hydrazine monohydrate (4.2 ml, 4.34 g, 86.66 mmol) was added via syringe and the solution was heated to 80° C. with stirring for 2 hours. An additional two drops of hydrazine monohydrate were added and the reaction was stirred for an additional 2 hours at 80° C. The reaction was cooled to room temperature. The volatiles were removed in vacuo with heating to 85° C. Tetrahydrofuran (10 ml) was added and the solids were filtered, collected, and dried.

Example 16

Synthesis of Guanidinium TFA

Trifluoroacetic acid (50.0 ml, 74.0 g, 649 mmol) was added to 500 ml of distilled water in a 4-liter beaker with stirring. Guanidine carbonate (58.5 g, 324.5 mmol) was added at room temperature in portions with stirring as to avoid bubbling over the sides of the beaker due to the evolution of carbon dioxide. The reaction was stirred at room temperature for 2 hours. The water was removed in vacuo with heating to approximately 90° C. for 4 hours. The product was recovered as a white crystalline solid.

Example 17

Synthesis of 1,2,4-Triazolium TFA 1,2,4-Triazole (2.0 g, 28.96 mmol) was dissolved in 5 ml of distilled water. Trifluoroacetic acid (2.15 ml, 3.30 g, 28.96 mmol) was added via syringe at room temperature and the reaction was stirred at room temperature for 1 hour. The water was removed in vacuo with heating to approximately 90° C. for 4 hours.

Example 18

Synthesis of 3-Amino-1,2,4-Triazolium TFA

3-Amino-1,2,4-triazole (1.27 g, 15.14 mmol) was dissolved in 5 ml of distilled water. Trifluoroacetic acid (1.12 ml, 15.14 mmol) was added via syringe at room temperature and the reaction was stirred at room temperature for 1 hour. The water was removed in vacuo with heating to approximately 90° C. for 4 hours.

Example 19

Synthesis of 4-Amino-1,2,4-Triazolium TFA

4-Amino-1,2,4-triazole (1.27 g, 15.14 mmol) was dissolved in 5 ml of distilled water. Trifluoroacetic acid (1.12 ml, 15.14 mmol) was added via syringe at room temperature and the reaction was stirred at room temperature for 1 hour. The water was removed in vacuo with heating to approximately 90° C. for 4 hours.

Example 20

Synthesis of 3,5-Diamino-1,2,4-Triazolium TFA 3,5-Diamino-1,2,4-triazole (1.50 g, 15.14 mmol) was dissolved in 5 ml of distilled water. Trifluoroacetic acid (1.12 ml, 15.14 mmol) was added via syringe at room temperature and the reaction was stirred at room temperature for 1 hour. The water was removed in vacuo with heating to approximately 90° C. for 4 hours.

Example 21

Synthesis of Bis(guanidinium) Tetrafluorosuccinate

Tetrafluorosuccinic acid (500 mg, 2.63 mmol) was dissolved in 10 ml of distilled water. Guanidine carbonate (474 mg, 2.63 mmol) was added at room temperature (carbon dioxide gas was evolved) and the reaction was stirred at room temperature for 2 hours. The water was removed in vacuo with heating to approximately 90° C. for 4 hours. The product was isolated as a white solid.

Example 22

Synthesis of BAG Tetrafluorosuccinate

Tetrafluorosuccinic acid (500 mg, 2.63 mmol) was dissolved in 10 ml of distilled water. Aminoguanidine bicarbonate (716 mg, 5.26 mmol) was added at room temperature (carbon dioxide gas was evolved) and the reaction was stirred at room temperature overnight. The water was removed in vacuo with heating to approximately 90° C. for 4 hours. The product was isolated as a slightly off-white solid.

Example 23

Synthesis of Bis(guanidinium) Oxalate

Oxalic acid (2.0 g, 22.20 mmol) was dissolved in 40 ml of distilled water. Guanidine carbonate (4.0 g, 22.20 mmol) was added at room temperature (carbon dioxide gas was evolved) and the reaction was stirred at room temperature for one hour. The water was removed in vacuo with heating to approximately 90° C. for 4 hours. The product was isolated as a white solid.

Example 24

Synthesis of Bis(aminoguanidinium) Oxalate

Oxalic acid (2.00 g, 22.20 mmol) was dissolved in 40 ml of distilled water. Aminoguanidine bicarbonate (6.05 g, 44.40 mmol) was added via syringe at room temperature (carbon dioxide gas was evolved) and the reaction was stirred at room temperature for 24 hours. The water was removed in vacuo with heating to approximately 90° C. for 4 hours. The product was isolated as a white solid.

Example 25

Synthesis of Bis(guanidinium) Malonate

Malonic acid (1.00 g, 9.61 mmol) was dissolved in 30 ml of distilled water. Guanidine carbonate (1.73 g, 9.61 mmol) was added via syringe at room temperature (carbon dioxide gas was evolved) and the reaction was stirred at room temperature for 24 hours. The water was removed in vacuo with heating to approximately 90° C. for 4 hours. The product was isolated as a white solid.

Example 26

Synthesis of Bis(aminoguanidinium) Malonate

Malonic acid (1.00 g, 9.61 mmol) was dissolved in 30 ml of distilled water. Guanidine carbonate (2.62 g, 19.22 mmol) was added at room temperature (carbon dioxide gas was evolved) and the reaction was stirred at room temperature for 24 hours. The water was removed in vacuo with heating to approximately 90° C. for 4 hours. The product was isolated as a white solid.

Example 27

Synthesis of Bis(guanidinium) L-Tartrate

L-Tartaric acid (2.00 g, 13.33 mmol) was dissolved in 5 ml of distilled water. Guanidine carbonate (2.40 g, 13.33 mmol) was added at room temperature (carbon dioxide gas was evolved) and the reaction was stirred at room temperature for 24 hours. The water was removed in vacuo with heating to approximately 90° C. for 4 hours. The product was isolated as a white solid.

Example 28

Synthesis of Bis(aminoguanidinium) L-Tartrate

L-Tartaric acid (20.00 g, 133.25 mmol) was dissolved in 200 ml of distilled water. Aminoguanidine bicarbonate (36.27 g, 266.51 mmol) was added in portions at room temperature (carbon dioxide gas was evolved) and the reaction was stirred at room temperature for 24 hours. The water was removed in vacuo with heating to approximately 90° C. for 4 hours. The product was isolated as a white solid.

Example 29

Synthesis of Bis(aminoguanidinium) DL-Tartrate

DL-Tartaric acid (500.00 g, 3.33 mol) was dissolved in 1.5 L of distilled water. Aminoguanidine bicarbonate (906.9 g, 6.66 mol) was added in portions at room temperature (carbon dioxide gas was evolved) and the reaction was stirred at room temperature for 18 hours. The water was removed in vacuo with heating to approximately 90° C. for 4 hours. The product was isolated as a white solid.

Example 30

Synthesis of Bis(aminoguanidinium) DL-Malate

DL-Malic acid (2.0 g, 14.92 mmol) was dissolved in 5 ml of distilled water. Aminoguanidine bicarbonate (4.06 g, 29.83 mmol) was added in portions at room temperature (carbon dioxide gas was evolved) and the reaction was stirred at room temperature for 18 hours. The water was removed in vacuo with heating to approximately 90° C. for 4 hours. The product was isolated as a white solid.

Example 31

Synthesis of Guanidinium Glycolate

Glycolic acid (3.0 g, 39.45 mmol) was dissolved in 15 ml of distilled water. Guanidine carbonate (3.55 g, 19.72 mmol) was added in portions at room temperature (carbon dioxide gas was evolved) and the reaction was stirred at room temperature for 4 hours. The water was removed in vacuo with heating to approximately 90° C. The product was isolated as a white solid.

Example 32

Synthesis of Tris(aminoguanidinium) Nitrilotriacetate

Nitrilotriacetic acid (1.0 g, 5.23 mmol) was dissolved in 10 ml of distilled water. Aminoguanidine bicarbonate (2.14 g, 15.69 mmol) was added in portions at room temperature (carbon dioxide gas was evolved) and the reaction was stirred at room temperature for three days. The water was removed in vacuo with heating to approximately 90° C. The product was isolated as a white solid.

Example 33

Synthesis of Aminoguanidinium Mucobromate

Mucobromic acid (2.0 g, 7.76 mmol) was dissolved in 10 ml of distilled water. Aminoguanidine bicarbonate (1.06 g, 7.76 mmol) was added in portions at room temperature (carbon dioxide gas was evolved) and the reaction was stirred at room temperature for 18 hours. The water was removed in vacuo with heating to approximately 90° C. The product was isolated as an off-white solid.

Example 34

Dent-Rate Testing of Formulations Including AGTFA

AGTFA was synthesized as described in Example 3. Explosive compositions that included AGTFA and an energetic material, such as RDX, HMX, or CL-20, were prepared by heating AGTFA to a temperature above its melting point (approximately 55° C.-60° C.), producing a melt of the AGTFA. The AGTFA-containing formulations are shown in Table 2. The energetic material was added to the melt phase and the AGTFA-containing formulations were poured into steel pipe or ordnance, as described below. The AGTFA-containing formulations were cooled to room temperature.

The detonation performance of the AGTFA-containing formulations was measured by a Dent and Rate test. A test sample of each of Formulations 1-14 was held in a steel pipe (3.7 cm diameter×14 cm length) having five holes drilled in the side for velocity switches from which the detonation velocity was calculated by regression analysis. The test sample was detonated using a booster that was 160 grams pentolite (50 pentaerythritol tetranitrate ("PETN"):50 TNT) and the depth of the dent made in a witness plate was measured. The dent depth was correlated to the denotation pressure, with a deeper dent corresponding to a higher pressure. The detonation velocity and dent depth were measured for each formulation, as shown in Table 2.

TABLE 2

Dent-rate Performance Data for AGTFA-containing Formulations.

| Formulation | AGTFA (%) | Energetic material | % Unground | % Ground | Total Nitramine (%) | Detonation Velocity (km/s) | Dent Depth (in) |
|---|---|---|---|---|---|---|---|
| 1 | 100 | — | — | — | — | 3.23 | 0 |
| 2 | 100 | — | — | — | — | 1.5 | 0 |
| 3 | 100 | — | 0 | 0 | 0 | 2.53 | 0 |
| 4 | 60 | RDX | 20 | 20 | 40 | 6.03 | 0.299 |
| 5 | 60 | RDX | 0 | 40 | 40 | 6.09 | 0.24 |
| 6 | 80 | RDX | 0 | 20 | 20 | 2.94 | 0 |
| 7 | 50 | RDX | 25 | 25 | 50 | 6.75 | 0.363 |
| 8 | 40 | RDX | 30 | 30 | 60 | 7.22 | 0.368 |
| 9 | 30 | RDX | 35 | 35 | 70 | 7.31 | 0.337 |
| 10 | 60 | HMX | 0 | 40 | 40 | 6.6 | 0.255 |
| 11 | 60 | HMX | 20 | 20 | 40 | 6.56 | 0.263 |
| 12 | 34 | HMX | 66 | 0 | 66 | 8.04 | 0.375 |
| 13 | 34 | HMX | 66 | 0 | 66 | 7.45 | 0.378 |
| 14 | 25 | CL-20 | 45 | 30 | 75 | 8.38 | 0.404 |

The formulations that included neat AGFTA did not detonate, as evidenced by the lack of dent in the witness plate. However, these formulations appeared to burn, as evidenced by the positive detonation velocity. As the amount of energetic material in the formulations increased, the detonation velocities and dent depths increase dramatically. Formulations 12 and 13 had plate dent depths and velocities approaching those of Composition B (detonation velocity equals approximately 7.2 km/s and dent depth equals approximately 0.41 in).

Formulation 7 (50% AGTFA and 50% RDX) was poured into 81 mm mortars and subjected to bullet impact, slow cook off, fast cook off, and grenade shape charge jet ("SCJ") testing. These tests were conducted by conventional techniques. Results of the testing are shown in Table 3.

TABLE 3

Results of bullet impact, slow cook off, fast cook off, and grenade SCJ testing.

| Insensitive Munition Test | Specifics | Result |
|---|---|---|
| Slow Cook Off | ~15° F./hour | No detonation reaction @ 306° F. |
| Fast Cook Off | | No detonation |
| 50 cal bullet impact | | Passed (no detonation) |
| 25 mm SCJ | | Passed (no detonation) |

While the invention may be susceptible to various modifications and alternative forms, specific embodiments have been described in detail herein. However, it should be understood that the invention is not intended to be limited to the particular forms disclosed. Rather, the invention is to cover all modifications, equivalents, and alternatives falling within the spirit and scope of the invention as defined by the following appended claims.

What is claimed is:

1. An ionic liquid selected from the group consisting of, aminoguanidinium hexafluoroglutarate, bis(aminoguanidinium) hexafluoroglutarate, guanidinium trifluoroacetate, aminoguanidinium trifluoroacetate, diaminoguanidinium trifluoroacetate, triaminoguanidinium trifluoroacetate, aminoguanidinium tetrafluorosuccinate, bis(aminoguanidinium) tetrafluorosuccinate, aminoguanidinium oxalate, aminoguanidinium:guanidinium oxalate, bis(aminoguanidinium) oxalate, bis(aminoguanidinium) malonate, aminoguanidinium:guanidinium malonate, aminoguanidinium L-tartrate, bis(aminoguanidinium) L-tartrate, bis(aminoguanidinium) DL-tartrate, aminoguanidinium glycolate, diaminoguanidinium acetate, triaminoguanidinium acetate, bis(aminoguanidinium) DL-malate, tris(aminoguanidinium) nitrilotriacetate, aminoguanidinium mucobromate, diaminoguanidinium.hydrochloric acid/urea, aminoguanidinium 5-aminotetrazolate, diaminoguanidinium 5-aminotetrazolate, triaminoguanidinium 5-aminotetrazolate, and combinations thereof.

2. A method of producing an ionic liquid, comprising:
reacting an anion source with a cation source, wherein the anion source is a compound selected from the group consisting of hexafluoroglutaric acid, trifluoroacetic acid, oxalic acid, L-tartaric acid, DL-malic acid, malonic acid, tetrafluorosuccinic acid, glycolic acid, nitrilotriacetate, mucobromic acid, 5-aminotetrazole, and 5-aminotetrazole monohydrate and the cation source is a compound selected from the group consisting of guanidine carbonate, aminoguanidine bicarbonate, diaminoguanidine.hydrochloric acid, and triaminoguanidine.hydrochloric acid when the cation source is selected from guanidine carbonate, the anion source is selected from triflouroacetic acid.

3. The ionic liquid of claim 1, wherein the ionic liquid comprises guanidinium trifluoroacetate.

4. The ionic liquid of claim 1, wherein the ionic liquid comprises aminoguanidinium trifluoroacetate.

5. The ionic liquid of claim 1, wherein the ionic liquid comprises guanidinium trifluoroacetate and aminoguanidinium trifluoroacetate.

6. The ionic liquid of claim 1, wherein the ionic liquid is a liquid.

7. The method of claim 2, wherein reacting an anion source with a cation source comprises reacting stoichiometric amounts of the anion source and the cation source.

8. The method of claim 2, wherein reacting an anion source with a cation source comprises reacting an excess of the anion source with the cation source.

9. The method of claim 2, wherein reacting an anion source with a cation source comprises reacting an excess of the cation source with the anion source.

10. The method of claim 2, wherein reacting an anion source with a cation source comprises reacting aminoguanidine bicarbonate and trifluoroacetic acid.

11. The method of claim 10, wherein reacting aminoguanidine bicarbonate and trifluoroacetic acid comprises reacting the aminoguanidine bicarbonate and trifluoroacetic acid at 70° C. to produce aminoguanidine trifluoroacetate.

12. The method of claim 10, wherein reacting aminoguanidine bicarbonate and trifluoroacetic acid comprises reacting the aminoguanidine bicarbonate and trifluoroacetic acid at from approximately 20° C. to approximately 25° C. to produce aminoguanidine trifluoroacetate.

13. The method of claim 2, wherein reacting an anion source with a cation source comprises reacting guanidine carbonate and trifluoroacetic acid.

14. The method of claim 13, wherein reacting guanidine carbonate and trifluoroacetic acid comprises reacting the guanidine carbonate and trifluoroacetic acid at from approximately 20° C. to approximately 25° C. to produce guanidine trifluoroacetate.

* * * * *

UNITED STATES PATENT AND TRADEMARK OFFICE
CERTIFICATE OF CORRECTION

PATENT NO. : 8,012,277 B2
APPLICATION NO. : 11/735105
DATED : September 6, 2011
INVENTOR(S) : Steven M. Nicolich et al.

Page 1 of 1

It is certified that error appears in the above-identified patent and that said Letters Patent is hereby corrected as shown below:

In the claims:
CLAIM 1, COLUMN 20, LINES 25, 26 change "diaminoguanidinium.hydrochloric acid/urea,"
to --diaminoguanidinium·hydrochloric acid/urea,--
CLAIM 2, COLUMN 20, LINES 40, 41 change "diaminoguanidine.hydrochloric acid,"
to --diaminoguanidine·hydrochloric acid,--
CLAIM 2, COLUMN 20, LINE 42, change ".hydrochloric acid," to --·hydrochloric acid,--

Signed and Sealed this
Twenty-second Day of October, 2013

Teresa Stanek Rea
*Deputy Director of the United States Patent and Trademark Office*